United States Patent
Gibson et al.

(10) Patent No.: US 10,532,114 B2
(45) Date of Patent: Jan. 14, 2020

(54) BIOMEDICAL MATERIALS

(71) Applicants: ApaTech Limited, Elstree, Hertfordshire (GB); University Court of the University of Aberdeen, Aberdeen, Aberdeenshire (GB)

(72) Inventors: Iain Ronald Gibson, Aberdeen (GB); Janet Mabel Scott Skakle, Aberdeen (GB); Nigel Smith, Norwich (GB); Thomas Buckland, Aylesbury (GB)

(73) Assignees: ApaTech Limited, Elstree, Hertfordshire (GB); University Court of the University of Aberdeen, Aberdeen, Aberdeenshire (GB)

( * ) Notice: Subject to any disclaimer, the term of this patent is extended or adjusted under 35 U.S.C. 154(b) by 291 days.

(21) Appl. No.: 15/418,304

(22) Filed: Jan. 27, 2017

(65) Prior Publication Data

US 2017/0136133 A1 May 18, 2017

Related U.S. Application Data

(62) Division of application No. 12/303,951, filed as application No. PCT/GB2007/002116 on Jun. 7, 2007, now Pat. No. 9,561,960.

(30) Foreign Application Priority Data

Jun. 7, 2006 (GB) .................................. 0611223.9

(51) Int. Cl.
*A61K 9/00* (2006.01)
*A61K 49/08* (2006.01)
(Continued)

(52) U.S. Cl.
CPC .............. *A61K 49/08* (2013.01); *A61K 49/00* (2013.01); *A61K 49/1803* (2013.01);
(Continued)

(58) Field of Classification Search
CPC ....................................................... A61K 49/08
See application file for complete search history.

(56) References Cited

U.S. PATENT DOCUMENTS

| 4,222,890 A | 9/1980 | Takahara et al. |
| 5,300,281 A | 4/1994 | McMillan et al. |

(Continued)

FOREIGN PATENT DOCUMENTS

| WO | WO9307905 A2 | 4/1993 |
| WO | WO9423649 A1 | 10/1994 |

(Continued)

OTHER PUBLICATIONS

Arcos et al., Crystal-Chemical Characteristics of Silicon-Neodymium Substituted Hydroxyapatites Studied by Combined X-ray and Neutron Powder Diffraction, Chem. Mater., 2005,17 (1), pp. 57-64.

(Continued)

*Primary Examiner* — Paul W Dickinson
(74) *Attorney, Agent, or Firm* — K&L Gates LLP (57) ABSTRACT

A synthetic calcium phosphate-based biomedical material comprising gadolinium. The material may comprises a compound having the general chemical formula: $Ca_{10-y}Gd_y(PO_4)_{6-x}(SiO_4)x(OH)_{2-c+y}$ where $0<x<1.3$ and $0<y<1.3$.

20 Claims, 3 Drawing Sheets

(51) Int. Cl.
  *A61K 49/00*   (2006.01)
  *C01B 25/32*   (2006.01)
  *A61K 49/18*   (2006.01)
  *A61L 27/02*   (2006.01)
  *A61L 27/42*   (2006.01)

(52) U.S. Cl.
  CPC ............ *A61L 27/025* (2013.01); *A61L 27/425* (2013.01); *C01B 25/32* (2013.01); *A61L 2430/02* (2013.01)

(56) References Cited

U.S. PATENT DOCUMENTS

| | | |
|---|---|---|
| 5,344,640 A | 9/1994 | Deutsch et al. |
| 5,595,724 A | 1/1997 | Deutsch et al. |
| 6,624,339 B1 | 9/2003 | Carpena et al. |
| 7,695,740 B2 | 4/2010 | Gibson et al. |
| 2004/0029699 A1 | 2/2004 | Lemaitre et al. |
| 2005/0287071 A1 | 12/2005 | Wenz |
| 2006/0078590 A1 | 4/2006 | Hermansson et al. |
| 2007/0196259 A1 | 8/2007 | Stark et al. |

FOREIGN PATENT DOCUMENTS

| | | | | |
|---|---|---|---|---|
| WO | WO 9622731 A1 * | 8/1996 | ......... | A61K 49/0428 |
| WO | WO9622731 A1 | 8/1996 | | |
| WO | WO1998008773 A1 | 3/1998 | | |
| WO | WO2004050131 A1 | 6/2004 | | |

OTHER PUBLICATIONS

Boyer et al., Synthesis of phosphate-silicate apatites at atmospheric pressure, Solid State Ionics, vol. 95, Issues 1-2, Feb. 2, 1997, pp. 121-129.
Carpena et al., Ca2+, PO, SiO44—coupled substitution in the apatitic structure: stability of the mono-silicated fluor-britholite, Comptes Rendus de l'Académie des Sciences—Series IIA—Earth and Planetary Science,vol. 333, Issue 7, Oct. 15, 2001, pp. 373-379.
Doat et al., Synthesis of luminescent bioapatite nanoparticles for utilization as a biological probe, Journal of Solid State Chemistry, vol. 177, Issues 4-5, Apr.-May 2004, pp. 1179-1187.
German Search Report dated Nov. 15, 2006 issued in the related German patent application No. 0611223.9.
ISR and WO dated Oct. 9, 2007, issued in the related International patent application No. PCT/GB2007/002116.
ITO, Silicate Apatites and Oxyapatites, The American Mineralogist, 1968, vol. 53, 890-907.
Kawajiri, Fundamentals and chemistry of the application of ear earth-containing hydroxyapatites as dental implant materials, Dep. Chem., Osaka Dent. Univ., Osaka, 573, japan, Shika Igaku (1988), 51(1), 75-96, XP-002453013.
Matsuda et al., ESR study of Gd3+ and Mn2+ ions sorbed on hydroxyapatite, Appl Radiat Isot. Feb. 2005;62(2):353-7.
Nakashima et al., Magnetic properties of gadolinium-doped beta-tricalcium phosphate, Journal of Alloys and Compounds, Elsevier Sequoia, Lausanne, CH, vol. 408-412, Feb. 9, 2006 (Feb. 9, 2006), pp. 761-765.
Patel et al., In vivo assessment of hydroxyapatite and silicate-substituted hydroxyapatite granules using an ovine defect model, J Mater Sci Mater Med. May 2005;16(5):429-40.
Rousselle, Etude de la formation du phosphate diphosphate de thorium (PDT) en milieu nitrique en vue d'une décontamination d'effluents de haute activité contenant des actinides, University of Paris, 2004, pp. 1, 6-12—Original and English translation.
Skakle, Applications of X-ray powder diffraction in materials chemistry, Chem Rec. 2005;5(5)252-62.

* cited by examiner

BIOMEDICAL MATERIALS

The present invention relates to biomedical materials and, in particular, to calcium phosphate bioceramics (eg apatite and hydroxyapatite) containing gadolinium as an MRI contrast agent.

The combined affects of an ageing population and greater expectations in the quality of life have resulted in an increasing global demand for orthopaedic implants for the replacement or augmentation of damaged bones and joints. In bone grafting current gold standards include the use of autograft and allograft but these methods are increasingly recognised as non-ideal due to limitations in supply and consistency. Ceramics have been considered for use as bone graft substitutes to replace or extend traditional bone grafts for over 30 years. In particular, calcium phosphates such as hydroxyapatite have been promoted as a result of their osteoinductive properties.

Accordingly, as surgical technique and medical knowledge continue to advance, there has been a growth in the demand for synthetic bone replacement materials. Consequently, there is an increasing interest in the development of synthetic bone replacement materials for the filling of both load bearing and non-load bearing osseous defects, such as in joint and facial reconstruction.

The biocompatibility of hydroxyapatite, coupled with the similarities between the crystal structure of hydroxyapatite and the mineral content of bone, has led to great interest in hydroxyapatite as a material for the augmentation of osseous defects. The apatite group of minerals is based on calcium phosphate, with stoichiometric hydroxyapatite having a molar ratio of Ca/P of 1.67. Hydroxyapatite has the chemical formula $Ca_{10}(PO_4)_6(OH)_2$.

Silicate-substituted hydroxyapatite compositions provide attractive alternatives to stoichiometric hydroxyapatite as a bone replacement material. Silicon has been shown to enhance the rate and quality of bone healing when combined with calcium phosphate bone grafts, resulting in faster bone bonding between implant and host. PCT/GB97/02325 describes a silicate-substituted hydroxyapatite material.

Nuclear magnetic resonance (NMR) is the absorption of electromagnetic radiation at a suitable precise frequency by a nucleus with a non-magnetic moment in an external magnetic field. NMR can be used for the accurate determination of nuclear moments. It can also be used in a sensitive form of magnetometer to measure magnetic fields. In medicine, magnetic resonance imaging (MRI) has been developed in which images of tissue are produced by magnetic-resonance techniques.

To enable clinicians to visualise tissue repair within a macroporous calcium phosphate implant, or an implant with a cavity or void, with MRI, it is routine to introduce a gadolinium contrast agent by the injection of a gadolinium-containing compound that will pass throughout the patient's blood stream. This can be associated with undesirable side effects and the process is also somewhat complicated and time-consuming. In addition, the process is not localised.

The present invention aims to address at least some of the problems associated with the prior art.

Accordingly, the present invention provides a synthetic calcium phosphate-based biomedical material comprising gadolinium.

At least some of the gadolinium is preferably in the form of $Gd^{3+}$ ions. The gadolinium ion is believed to substitute for the calcium ion in the calcium phosphate (eg apatite or hydroxyapatite) lattice.

Advantageously, the calcium phosphate composition according to the present invention contains gadolinium ions (eg $Gd^{3+}$) that are incorporated into the calcium phosphate crystal structure. The gadolinium ions in the calcium phosphate material enable it to act as a contrast agent in MRI.

The biomedical material preferably also further comprises silicon and/or silicate. This has been found to improve the osteoinductive characteristics of the material. If present, the silicate ion is believed to substitute for the phosphate ion in the hydroxyapatite lattice.

For the avoidance of doubt, the term silicate-substituted as used herein also encompasses silicon-substituted. Likewise, silicon-substituted as used herein also encompasses silicate-substituted.

The calcium phosphate-based biomedical material will typically comprise hydroxyapatite or apatite.

In a preferred embodiment of the present invention, the material comprises a compound having the general chemical formula:

$$Ca_{10-y}Gd_y(PO_4)_{6-x}(SiO_4)_x(OH)_{2-x+y}$$

Preferably, $0<x<1.3$, more preferably $0.5<x<1.1$.

Preferably, $0<y<1.3$. It is also preferable that $x \geq y$.

In one aspect, $0.001<y<1.1$, more preferably $0.1<y<1.3$. Such a composition may be used diluted with another bone material (eg a calcium phosphate material), either synthetic or allograft or autograft, as an MRI contrast agent with gadolinium ions substituted into the crystal structure of the biomedical material acting as the active contrast agent.

In another aspect, $0<y<0.05$, more preferably $0<y<0.025$. Such a composition may be used undiluted.

In one embodiment of the present invention, where an essentially phase pure material is required, the phase purity of the material is preferably at least 95%, more preferably at least 97%, still more preferably at least 99%. In this case the material is substantially free of any secondary phases. It will be appreciated that unavoidable impurities may, however, be present. As will be appreciated, the phase purity of the biomedical material can be measured by conventional X-ray diffraction techniques.

In another embodiment, where the presence of secondary phases does not present a problem, the material may further comprise one or more secondary phases such as, for example, tricalcium phosphate (eg $\alpha$-TCP and/or $\beta$-TCP), calcium silicate and tetracalcium phosphate. Accordingly, the present invention also provides for biphasic and multi-phase materials. The secondary phases may be present in an amount of up to 60 wt. %, more typically up to 40 wt. %, still more typically up to 20 wt. %.

The present invention also provides a biomedical material comprising a synthetic gadolinium-silicate co-substituted calcium phosphate-based material. Examples include gadolinium-silicate co-substituted hydroxyapatite and apatite materials. The preferred features described above are also applicable either singularly or in combination to this aspect of the present invention.

The biomedical material according to the present invention may be used as a synthetic bone material, a bone implant, a bone graft, a bone substitute, a bone scaffold, a filler, a coating or a cement. The biomedical material may be provided in a porous or non-porous form. The biomedical material may be provided in the form of a composite material, for example in conjunction with a biocompatible polymer.

The present invention involves the synthesis of a calcium phosphate composition that contains gadolinium ions that are incorporated into the calcium phosphate crystal structure. The amount of gadolinium ions that are required in the calcium phosphate material to enable it to act as a contrast agent in MRI is quite low. The material according to the present invention can therefore be used in a number of ways as described above, i.e. undiluted or mixed with another bone material.

The biomedical material according to the present invention may be prepared by an aqueous precipitation method or a solid-state method such as, for example, a hydrothermal method or a sol-gel method. The aqueous precipitation technique is, however, preferred. Accordingly, the present invention also provides a process for the synthesis of a calcium phosphate-based material comprising gadolinium and optionally silicon, the process comprising: providing calcium or a calcium-containing compound, a gadolinium-containing compound, a phosphorus-containing compound and optionally a silicon-containing compound; and forming a precipitate by reacting the compounds in an aqueous phase at an alkali pH.

The process according to the present invention is preferably an aqueous precipitation process.

The process may be used to synthesise hydroxyapatite and apatite materials containing gadolinium and also preferably silicon.

Preferably, the calcium-containing compound comprises a calcium salt. The calcium salt may, for example, be selected from one or more of calcium hydroxide, calcium oxide, calcium chloride, calcium nitrate and/or calcium nitrate hydrate.

Preferably, the gadolinium-containing compound comprises one or both of gadolinium chloride and/or gadolinium nitrate, preferably $Gd(NO_3)_3 \cdot XH_2O$.

The gadolinium is preferably present in the biomedical material (i.e. the final product) in an amount of up to 13 weight percent, more preferably up to 12 weight percent. This is typical if the material is an essentially phase pure material as discussed above. On the other hand, if the material comprises one or more secondary phases, then the amount of gadolinium in the material may exceed 13 weight percent and may be present in an amount of up to 20 weight percent.

Preferably, the phosphorus-containing compound is selected from one or both of a phosphate salt and/or a phosphoric acid. More preferably, the phosphorus-containing compound is selected from one or both of ammonium phosphate and/or phosphoric acid.

Preferably, the (optional) silicon-containing compound comprises a silicate. More preferably, the silicate is selected from one or both of tetraethyl orthosilicate (TEOS) and/or silicon acetate.

The silicate is preferably present in the material (i.e. the final product) in an amount of up to 13 weight percent (which correlates to 4 weight percent as silicon), more preferably up to 12 weight percent (which correlates to 3.66 weight percent silicon). Again, this is typical if the material is an essentially phase pure material as discussed above. On the other hand, if the material comprises one or more secondary phases, then the amount of silicate in the material may exceed 13 weight percent and may be present in an amount of up to 20 weight percent.

In one embodiment, the silicon-containing compound and the gadolinium-containing compound are preferably supplied in substantially equimolar quantities with respect to the amount of silicon and the quantity of the gadolinium. In an alternative embodiment, the silicon-containing compound is supplied in a greater molar quantity than the gadolinium-containing compound, with respect to the quantity of silicon and the quantity of the gadolinium.

The process according to the present invention is preferably carried out at an alkaline pH. Preferably, the pH is from 8 to 13. More preferably, the pH is from 10 to 12.

In order to adjust the pH of the solution to the desired pH, an alkali is preferably added to the solution. The alkali may be, for example, ammonium hydroxide or concentrated ammonia.

After the precipitate has been formed it may be dried, heated and/or sintered. The precipitate may be heated and/or sintered to a temperature in the range of from 800° C. to 1500° C., preferably from 1000° C. to 1350° C., more preferably from 1200° C. to 1300° C.

The process according to the present invention preferably comprises first forming under ambient conditions (although this step can be performed at a temperature up to about 100° C.) an aqueous suspension comprising calcium or the calcium-containing compound (e.g. $Ca(OH)_2$) and the gadolinium-containing compound (e.g. $Gd(NO_3)_3 \cdot XH_2O$). Next, an aqueous solution of the phosphorus-containing compound (e.g. $H_3PO_4$) is slowly added to the suspension with stirring. Finally, and if desired, an aqueous solution of the silicon-containing compound (e.g. $Si(OC_2H_5)_4$=TEOS) is added slowly with stirring (instead, the aqueous solution of the phosphorus-containing compound can be mixed with the aqueous solution of the silicon-containing compound, and the combination then added slowly with stirring the suspension). The pH is monitored and maintained at an alkali pH, preferably from 11 to 13, using, for example, concentrated ammonia solution. The total mixture is then left to age and precipitate, which typically takes up to 12 to 24 hours.

Once the precipitate has been formed and aged it may be dried, heated and/or sintered. Preferably, it is first dried by heating it to a temperature of up to 100° C. This may then be followed by heating a temperature in the range of from 800° C. to 1500° C., more preferably from 1000° C. to 1350° C., and even more preferably from 1200° C. to 1300° C., in order to sinter the material. The dried precipitate is preferably ground into a powder prior to the sintering step.

The aforementioned process may be used to prepare an essentially phase pure material as herein described.

If it is desired to produce a biphasic or multiphase material, a number of steps may be used independently or in combination. For example, a deficient amount of the calcium-containing compound (e.g. $Ca(OH)_2$) and the gadolinium-containing compound (e.g. $Gd(NO_3)_3 \cdot XH_2O$) may be added, which promote the precipitation of a gadolinium/silicate co-substituted cation-deficient apatite composition. This will form a biphasic gadolinium/silicate co-substituted composition on heating.

The process according to the present invention may involve diluting the thus formed calcium phosphate-based gadolinium-containing material with another material (eg a gadolinium-free material) to produce a sufficient gadolinium cation concentration that will act as a contrast agent for MRI. The gadolinium-free material may be, for example, a calcium phosphate-based material or polymer material. Alternatively, it may be allograft or autograft bone, demineralised bone matrix, or a synthetic or natural material for the repair or replacement of bone.

The present invention also provides a method of improving MRI contrast in a calcium phosphate material (eg hydroxyapatite or apatite), which method comprises substituting $Gd^{3+}$ into the lattice.

The present invention also provides a method of improving MRI contrast in a silicon-substituted calcium phosphate material (eg hydroxyapatite or apatite), which method comprises co-substituting $Gd^{3+}$ into the lattice.

The present invention also provides for the use of gadolinium substituted in a synthetic hydroxyapatite or apatite lattice to improve MRI contrast.

The present invention also provides for the use of gadolinium co-substituted with silicate in a synthetic hydroxyapatite or apatite lattice to improve MRI contrast.

The present invention will now be described further with reference to the following preferred embodiments.

To enable an improvement in MRI contrast the present invention provides a substitution method, whereby gadolinium is substituted (or co-substituted with silicate ions) into the calcium phosphate lattice (eg hydroxyapatite or apatite).

Two distinct mechanisms are possible. The first essentially negates the loss of hydroxyl (OH) groups from the hydroxyapatite lattice to balance charge, as the equimolar substitution of gadolinium and silicate ions for calcium and phosphate ions balances charge:

$$Gd^{3+}+SiO_4^{4-}\rightarrow Ca^{2+}+PO_4^{3-} \quad (1)$$

This may be summarised by the general equation:

The second substitution, where proportionally less gadolinium ions are co-substituted with silicate ions, which results in the reduction in the level of OH groups to balance the charge (for an example where the molar amount of gadolinium is half the molar amount of silicate being substituted):

$$0.5Gd^{3+}+SiO_4^{4-}\rightarrow 0.5Ca^{2+}+PO_4^{3-}+0.5OH^- \quad (2)$$

This may be summarised by the general equation:

(for this mechanism, y<x)

As for other ionic substitutions in the hydroxyapatite lattice, these substitutions have limits. When the levels of substitution pass these limits, the composition becomes thermally unstable during sintering, and phase decomposition of the hydroxyapatite occurs, leading to the formation of secondary phases. The co-substituted method according to the present invention may be used to increase the limit of silicate substitution into the hydroxyapatite lattice, without resulting in phase decomposition after sintering at typical temperatures (approximately 1200° C. or more), to a maximum of approximately 12 wt. % silicate ions (or 3.66 wt. % silicon). After this limit has been reached, secondary phases are produced. For certain applications, an essentially phase pure material is desired, and so the maximum of approximately 12 wt. % silicate ions will be adopted. For other applications, the presence of secondary phases may actually be desired (or may not present a problem), and the limit of approximately 12 wt. % silicate may then be exceeded.

The present invention will now be further described with reference to the following Examples and the accompanying drawings, provided by way of example, in which.

EXAMPLE 1

Synthesis of $Gd^{3+}/SiO_4^{4-}$ Co-Substituted Hydroxyapatite (x=y=1.0)

The following method describes the synthesis of approx. 10 g of a $Gd^{3+}/SiO_4^{4-}$ co-substituted hydroxyapatite by an aqueous precipitation method with the following substitution mechanism:

where x=y=1.0

$CaCO_3$ was first de-carbonated overnight (16 hours) in a furnace at 900° C. The resulting CaO was then removed from the furnace and placed in a dessicator to cool. 5.0543 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to from $Ca(OH)_2$.

Meanwhile, 4.5141 g $Gd(NO_3)_3.6H_2O$ (GNH) was added to a beaker containing approx. 100 ml deionised water and mixed well until the GNH had completely dissolved. The GNH solution was then slowly poured into the $Ca(OH)_2$ suspension and this suspension was left to stir for approx. 15 minutes.

Figure 1:
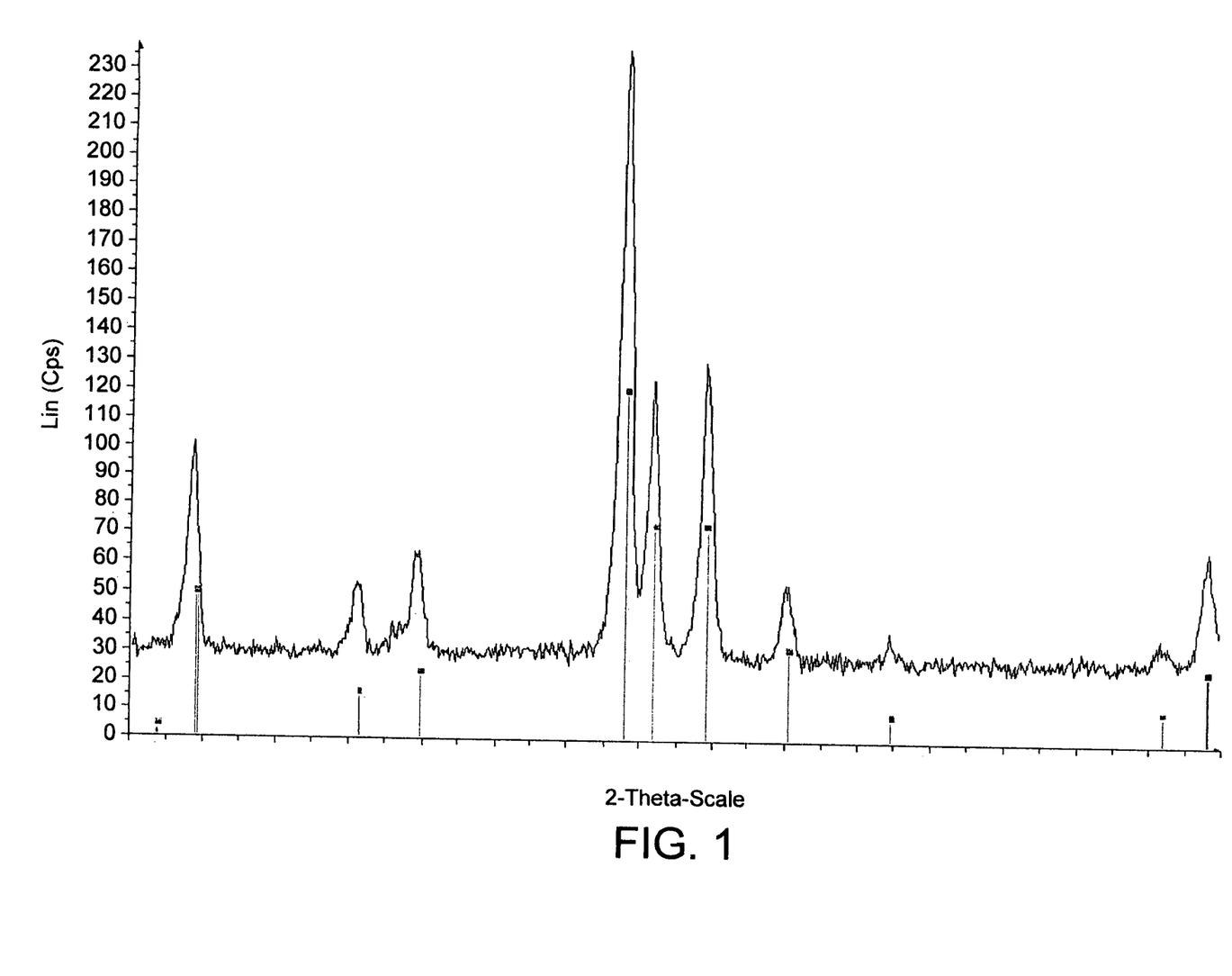
FIG. 1 is an X-ray diffraction pattern obtained for Example 1 compared with the ICDD (#09-0432) standard pattern for hydroxyapatite.

5.7664 g $H_3PO_4$ (85% assay) was diluted with approx. 100 ml deionised water. This solution was poured into a dropping funnel and added drop-wise to the stirring Ca(OH)₂/GNH suspension over a period of approx. 70 minutes. After complete addition of the $H_3PO_4$ solution, 2.1278 g $Si(OC_2H_5)_4$ (TEOS) was diluted with approx. 100 ml deionised water and this solution was poured into a dropping funnel and added drop-wise to stirring $Ca(OH)_2$/GNH/ $H_3PO_4$ mixture over a period of approx. 70 minutes. The pH of the stirring solution was monitored throughout the addition of the $H_3PO_4$ and TEOS solutions and was maintained at pH12 by the addition of concentrated ammonia solution; in total, approx. 100 ml was added. After complete addition of the TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 5 and 10° C./min respectively. The sintered powder was then analysed using X-ray diffraction to confirm the phase purity. A Bruker D8 diffractometer was used to collect data from 25 to 40° 2θ with a step size of 0.02° and a count time of 9.5 secs/step. The diffraction pattern obtained was compared with the ICDD (#09-0432) standard pattern for hydroxyapatite. All the diffraction peaks for the sintered $Gd^{3+}/SiO_4^{4-}$ co-substituted hydroxyapatite matched the peaks of the ICDD standard, with no additional peaks observed, indicating that the composition produced by this method was a single-phase material with a hydroxyapatite-like structure (see FIG. 1).

0.2503 g of this $Gd^{3+}/SiO_4^{4-}$ co-substituted hydroxyapatite was diluted by mixing, in a pestle and mortar, with 4.7505 g of a $SiO_4^{4-}$ substituted hydroxyapatite to give a powder containing 5 wt % $Gd^{3+}/SiO_4^{4-}$ co-substituted hydroxyapatite. Similarly, 0.0124 g of the $Gd^{3+}/SiO_4^{4-}$ co-substituted hydroxyapatite was mixed with 4.9879 g of a $SiO_4^{4-}$ substituted hydroxyapatite to give a powder containing 0.25 wt % $Gd^{3+}/SiO_4^{4-}$ co-substituted hydroxyapatite. Approx. 5 ml deionised water was added to each of these powders to form pastes. Magnetic Resonance Imaging (MRI) was then used to assess the effect of $Gd^{3+}$ substitution on the MRI activity of the hydroxyapatite materials. Materials that have little or no MRI activity appear as darkened areas in the resulting image. Those that are MRI active will in contrast appear bright. The sample containing 5 wt % $Gd^{3+}/SiO_4^{4-}$ co-substituted hydroxyapatite was found to have an improved contrast, i.e. appeared brighter, than a pure hydroxyapatite. However, the contrast of the 0.25 wt % $Gd^{3+}/SiO_4^{4-}$ co-substituted hydroxyapatite was found to be even greater than that of the 5 wt % $Gd^{3+}/SiO_4^{4-}$ co-substituted hydroxyapatite.

EXAMPLE 2

Synthesis of $Gd^{3+}/SiO_4^{4-}$ Co-Substituted Hydroxyapatite (x=1.0, y=0.5)

The following method describes the synthesis of approx. 10 g of a $Gd^{3+}/SiO_4^{4-}$ co-substituted hydroxyapatite by an aqueous precipitation method with the following substitution mechanism:

$$Ca_{10-y}Gd_y(PO_4)_{6-x}(SiO_4)_x(OH)_{2-x+y}$$

where x=1.0, y=0.5

$CaCO_3$ was first de-carbonated overnight (16 hours) in a furnace at 900° C. The resulting CaO was then removed from the furnace and placed in a dessicator to cool. 5.3284 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to from $Ca(OH)_2$. Meanwhile, 2.2589 g $Gd(NO_3)_3.6H_2O$ (GNH) was added to a beaker containing approx. 100 ml deionised water and mixed well until the GNH had completely dissolved. The GNH solution was then slowly poured into the $Ca(OH)_2$ suspension and this suspension was left to stir for approx. 15 minutes.

Figure 2:
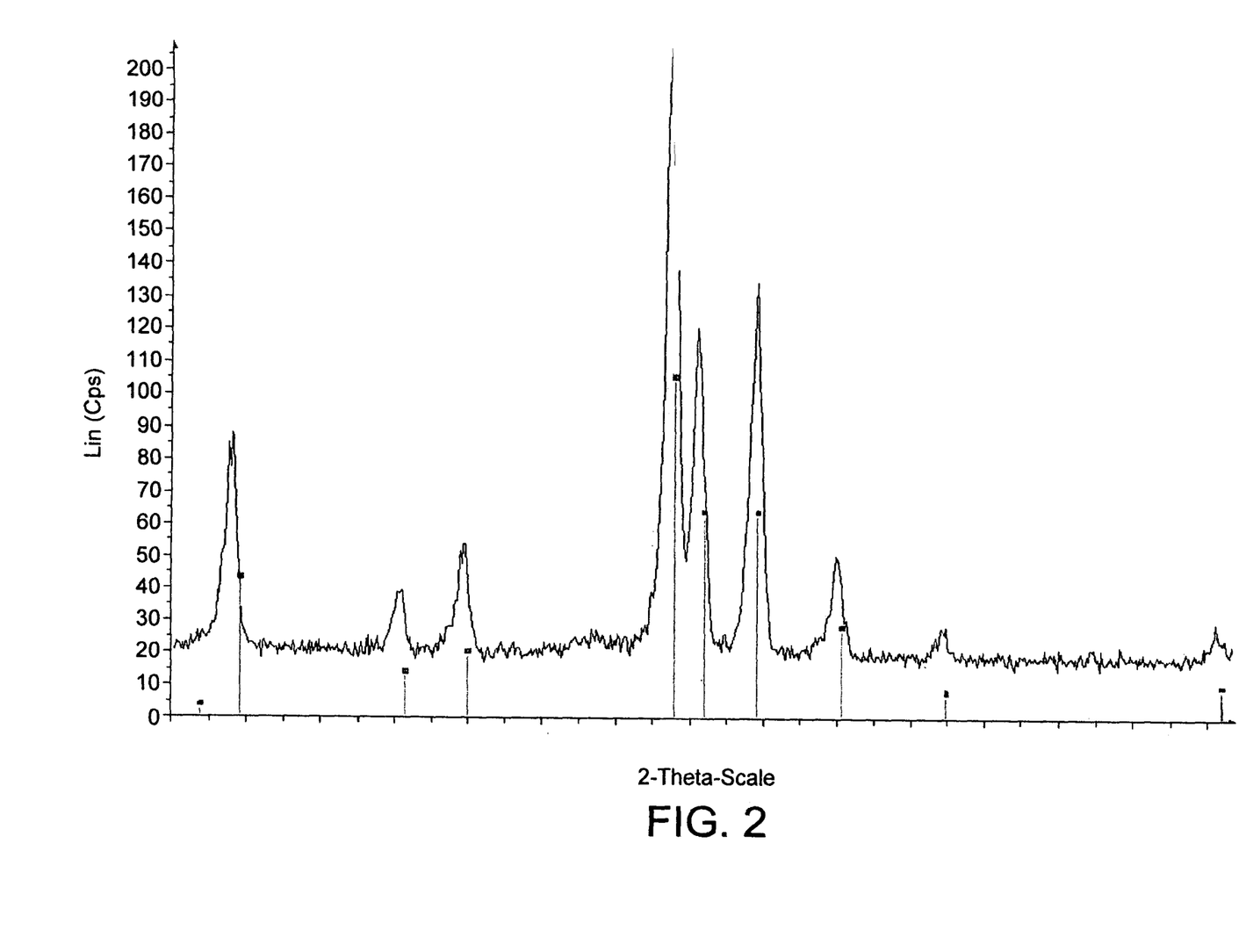
FIG. 2 is an X-ray diffraction pattern obtained for Example 2 compared with the ICDD (#09-0432) standard pattern for hydroxyapatite.

5.7645 g $H_3PO_4$ (85% assay) was diluted with approx. 100 ml deionised water. This solution was poured into a dropping funnel and added drop-wise to the stirring Ca(OH)$_2$/GNH suspension over a period of approx. 90 minutes. After complete addition of the $H_3PO_4$ solution, 2.1330 g $Si(OC_2H_5)_4$ (TEOS) was diluted with approx. 100 ml deionised water and this solution was poured into a dropping funnel and added drop-wise to stirring $Ca(OH)_2$/GNH/$H_3PO_4$ mixture over a period of approx. 75 minutes. The pH of the stirring solution was monitored throughout the addition of the $H_3PO_4$ and TEOS solutions and was maintained at pH12 by the addition of concentrated ammonia solution; in total, approx. 50 ml was added. After complete addition of the TEOS solution, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 5 and 10° C./min respectively. The sintered powder was then analysed using X-ray diffraction to confirm the phase purity. A Bruker D8 diffractometer was used to collect data from 25 to 40° 2θ with a step size of 0.02° and a count time of 9.5 secs/step. The diffraction pattern obtained was compared with the ICDD (#09-0432) standard pattern for hydroxyapatite. All the diffraction peaks for the sintered $Gd^{3+}/SiO_4^{4-}$ co-substituted hydroxyapatite matched the peaks of the ICDD standard, with no additional peaks observed, indicating that the composition produced by this method was a single-phase material with a hydroxyapatite-like structure (see FIG. 2).

EXAMPLE 3

Synthesis of $Gd^{3+}/SiO_4^{4-}$ Co-Substituted Hydroxyapatite/Tricalcium Phosphate Biphasic Mixture (x=1.1, y=1.1)

The following method describes the synthesis of approx. 10 g of a $Gd^{3+}/SiO_4^{4-}$ co-substituted hydroxyapatite/tricalcium phosphate biphasic mixture by an aqueous precipitation method with the following substitution mechanism:

$$Ca_{10-y}Gd_y(PO_4)_{6-x}(SiO_4)_x(OH)_{2-x+y}$$

where x=1.1, y=1.1

To produce a gadolinium/silicate co-substituted biphasic composition, rather than a single phase gadolinium/silicate co-substituted hydroxyapatite composition (described in Example 1), a deficient amount of $Ca(OH)_2$ and GNH was added, which promoted the precipitation of a gadolinium/silicate co-substituted cation-deficient apatite composition. This will form a biphasic gadolinium/silicate co-substituted composition on heating.

$CaCO_3$ was first de-carbonated overnight (16 hours) in a furnace at 900° C. The resulting CaO was then removed from the furnace and placed in a dessicator to cool. 4.9978 g CaO was added to a beaker containing approx. 100 ml deionised water in an ice bath. After complete addition of the CaO, the beaker was removed from the ice bath and placed on a stirrer. The suspension was left to stir for approx. 10 minutes; the CaO will undergo hydration to form $Ca(OH)_2$. Meanwhile, 4.9696 g $Gd(NO_3)_3.6H_2O$ (GNH) was added to a beaker containing approx. 100 ml deionised water and was mixed until the GNH had completely dissolved. The GNH solution was then slowly poured into the $Ca(OH)_2$ suspension and this suspension was left to stir for approx. 15 minutes.

5.6500 g $H_3PO_4$ (85% assay) was diluted with approx. 100 ml deionised water and this solution was poured into a dropping funnel and added drop-wise to the stirring Ca(OH)$_2$/GNH suspension over a period of approx. 80 minutes. After complete addition of the $H_3PO_4$ solution, 2.3402 g $Si(OC_2H_5)_4$ (TEOS) was diluted with approx. 100 ml deionised water and this solution was poured into a dropping funnel and added drop-wise to stirring $Ca(OH)_2$/GNH/$H_3PO_4$ mixture over a period of approx. 75 minutes. The pH of the stirring solution was monitored throughout the addition of the $H_3PO_4$ and TEOS solutions and was maintained at pH12 by the addition of concentrated ammonia solution; in total, approx. 50 ml was added. After complete addition of the $H_3PO_4$ and TEOS solutions, the total mixture was left to stir for a further 2 hours before being left to age and precipitate overnight (approximately 16 hours). The precipitate was then filtered, dried at 80° C. for 24 hours, and ground to form a fine powder. Approximately 3 g of the dried powder was placed in a platinum crucible and sintered in a furnace at 1200° C. for 2 hours, using heating and cooling rates of 5 and 10° C./min, respectively.

Figure 3:
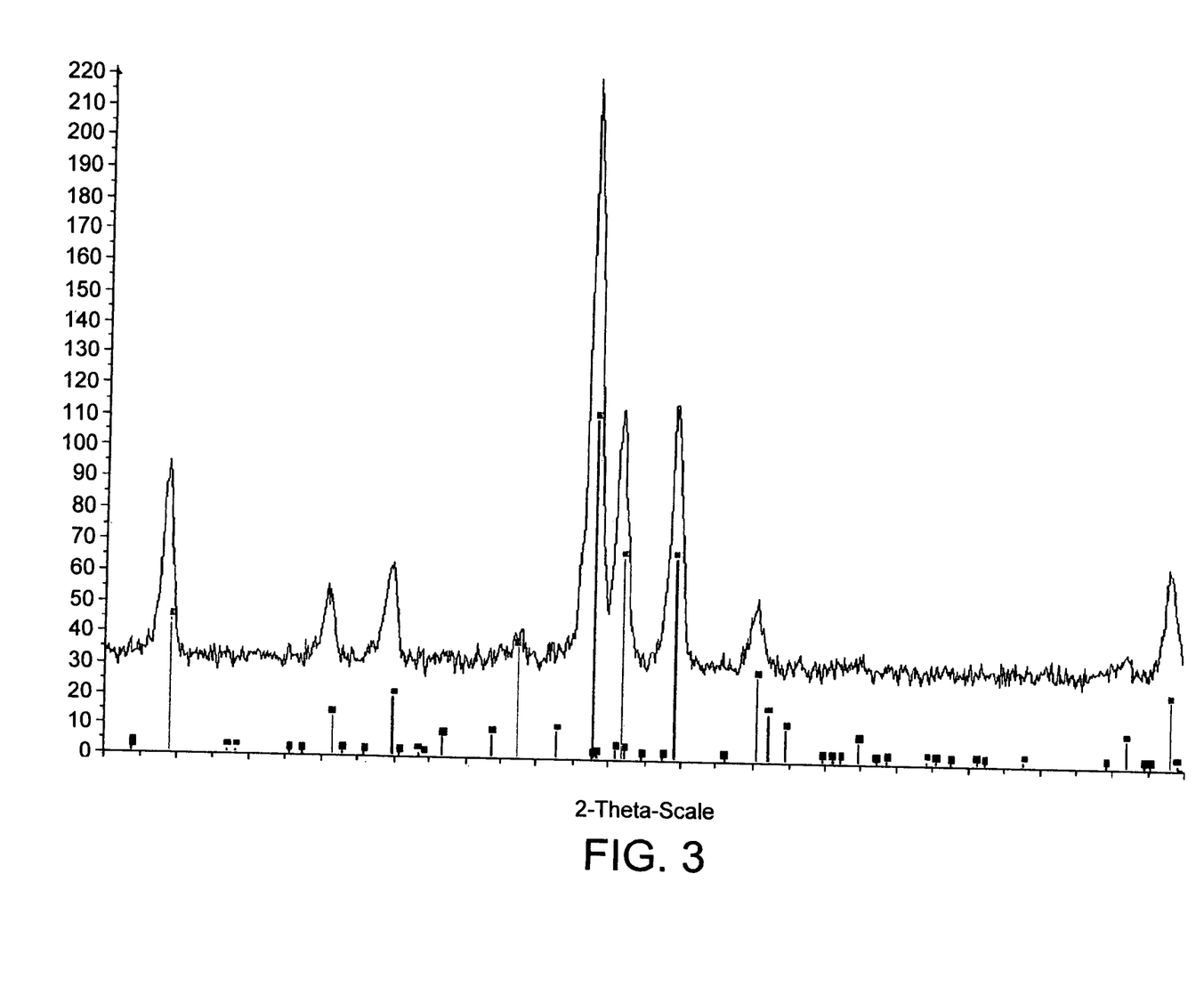
FIG. 3 is an X-ray diffraction pattern obtained for Example 3 compared with the ICDD (#09-0432) standard pattern for hydroxyapatite and (#09-0359) standard pattern for alpha-tricalcium phosphate.

The sintered powder was then analysed using X-ray diffraction to confirm the phase purity. A Bruker D8 diffractometer was used to collect data from 25 to 40° 2θ with a step size of 0.02° and a count time of 9.5 secs/step. The diffraction pattern obtained was compared with the ICDD (#09-0432) standard pattern for hydroxyapatite and (#09-0359) standard pattern for alpha-tricalcium phosphate. All the diffraction peaks for the sintered $Gd^{3+}/SiO_4^{4-}$ co-substituted hydroxyapatite matched the peaks of the ICDD standard, matching both the hydroxyapatite phase and the alpha-tricalcium phosphate phase, indicating that the composition produced by this method was a biphasic materials (see FIG. 3). Comparing the intensities of the most intense peaks of the hydroxyapatite and the alpha-tricalcium phosphate phases, the amount of hydroxyapatite is approximated as 84%, and the amount of tricalcium phosphate as 16%.

EXAMPLE 4

Use of a $Gd^{3+}/SiO_4^{4-}$ Co-Substituted Hydroxyapatite (x=y=1.0) in a Calcium Phosphate Composition to Enhance MRI, Contrast in a Bone Graft Material

To enable clinicians to visualise tissue repair within a macroporous calcium phosphate implant, or an implant with a cavity or void, with MRI, a surgeon would have to introduce a gadolinium contrast agent, normally by the injection of a gadolinium-containing compound that will pass throughout the patient's blood stream. The present invention provides for the synthesis of a calcium phosphate composition that contains gadolinium ions that are actually incorporated into the calcium phosphate crystal structure. The amount of gadolinium ions that are required in the calcium phosphate material to enable it to act as a contrast agent in MRI is quite low. The materials and methods described herein can therefore be used in one of two ways. Firstly, a calcium phosphate material such as that described in Example 1 can be prepared but with a very small value of x, typically x=0.0001 to 0.05; this material could then be used to construct the entire implant, and would contain sufficient gadolinium to act as a contrast agent in MRI. Alternatively, a calcium phosphate material such as that described in Example 1 can be prepared with a large value of x, such as x=1. This material could then be mixed with an appropriate amount of gadolinium-free calcium phosphate implant material, to effectively dilute the gadolinium-substituted calcium phosphate (with x=1) to an appropriate final concentration of gadolinium, for example in a 1:1000 ratio by weight of gadolinium-substituted calcium phosphate (with x=1) to gadolinium-free calcium phosphate implant material. Alternatively, the gadolinium-substituted calcium phosphate (e.g. with x=1) could be mixed with another synthetic bone replacement material, or with autograft or allograft bone, or with another bone replacement material of natural or synthetic origins.

As an example, the following compositions were prepared:

Samples (5 g), as sintered powders with particle sizes ranging from 10 to 500 microns, were placed in a small plastic sealable bag, and 7.5 g of water was added to form a paste like consistency. The bag was sealed, rolled up to form a cylindrical shaped sample, then covered in cling film. The samples were then fixed with tape onto a plastic bottle containing a dilute nickel chloride phantom solution, and placed in a 1 Tesla MRI. Gadolinium-substituted calcium phosphate with x=1 (as described in Example 1) was mixed with gadolinium-free calcium phosphate to provide a final concentration of Gd of approximately 0.25 wt % (A). As a comparison, a Gadolinium-substituted calcium phosphate (as described in Example 1) was prepared with x=0.02, corresponding to a gadolinium content of approximately 0.25 wt % (B). As controls, samples were prepared of gadolinium-free calcium phosphate (C) and Gadolinium-substituted calcium phosphate with x=1 (as described in Example 1) mixed with gadolinium-free calcium phosphate to provide a final concentration of Gd of approximately 5 wt % (D). The contrast observed for samples A and B were similar and were significantly enhanced compared to the two control samples C and D.

The present invention enables gadolinium to be substituted (or co-substituted with silicon) into the calcium phosphate (eg hydroxyapatite or apatite) lattice. As a consequence, the MRI contrast of the material can be improved. The synthetic biomedical material still closely matches the chemical composition of bone mineral. The present invention also enables the production of phase-pure, biphasic and multiphase materials.

The invention claimed is:
1. A method of improving MRI contrast in a calcium phosphate material comprising a calcium phosphate lattice, which method comprises substituting $Gd^{3+}$ into the lattice to produce a calcium phosphate material having the chemical formula:

wherein 0<x<1.1 and 0<y<1.3.

2. A method comprising:
   magnetic resonance imaging a biomedical material comprising a gadolinium substituted calcium phosphate lattice having the chemical formula:

wherein 0<x<1.1 and 0<y<1.3.

3. The method according to claim 1, wherein the phase purity of the calcium phosphate material, as measured by X-ray diffraction using the whole pattern method, is at least 95%.

4. The method according to claim 1, wherein 0.001<y<1.1.

5. The method according to claim 1, wherein 0.1<y<1.3.

6. The method according to claim 1, wherein 0<y<0.001.

7. The method according to claim 1, wherein 0<y<0.0005.

8. The method according to claim 1, wherein x≥y.

9. The method according to claim 1, wherein the gadolinium ion substitutes for the calcium ion in the calcium phosphate lattice.

10. The method according to claim 1, wherein the silicate ion substitutes for the phosphate ion in the calcium phosphate lattice.

11. The method according to claim 2, wherein the wherein the phase purity of the calcium phosphate material, as measured by X-ray diffraction using the whole pattern method, is at least 95%.

12. The method according to claim 2, wherein 0.001<y<1.1.

13. The method according to claim 2, wherein 0.1<y<1.3.

14. The method according to claim 2, wherein 0<y<0.001.

15. The method according to claim 2, wherein 0<y<0.0005.

16. The method according to claim 2, wherein x≥y.

17. The method according to claim 2, wherein the gadolinium ion substitutes for the calcium ion in the calcium phosphate lattice.

18. The method according to claim 2, wherein the silicate ion substitutes for the phosphate ion in the calcium phosphate lattice.

19. The method according to claim 2, wherein the method is method of visualizing tissue repair.

20. The method according to claim 2, wherein the method is a method of visualizing an implant with a cavity or void.

* * * * *